(12) United States Patent
Ramasamy et al.

(10) Patent No.: US 11,560,508 B2
(45) Date of Patent: Jan. 24, 2023

(54) EPOXIDIZED FATTY ACID METHYL ESTER AS PRIMARY EMULSIFIER FOR INVERT EMULSION OIL BASED MUD

(71) Applicant: SAUDI ARABIAN OIL COMPANY, Dhahran (SA)

(72) Inventors: Jothibasu Ramasamy, Dhahran (SA); Vikrant Wagle, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 166 days.

(21) Appl. No.: 16/932,035

(22) Filed: Jul. 17, 2020

(65) Prior Publication Data
US 2022/0017806 A1 Jan. 20, 2022

(51) Int. Cl.
C09K 8/28 (2006.01)
B01F 23/41 (2022.01)
C07D 303/42 (2006.01)
C07D 407/06 (2006.01)
C07D 407/14 (2006.01)

(52) U.S. Cl.
CPC ............ C09K 8/28 (2013.01); B01F 23/41 (2022.01); C07D 303/42 (2013.01); C07D 407/06 (2013.01); C07D 407/14 (2013.01); B01F 23/4142 (2022.01)

(58) Field of Classification Search
None
See application file for complete search history.

(56) References Cited

U.S. PATENT DOCUMENTS

| | | | |
|---|---|---|---|
| 4,244,829 A | 1/1981 | Coupland et al. |
| 5,252,554 A | 10/1993 | Mueller et al. |
| 9,127,192 B2 | 9/2015 | Maghrabi et al. |
| 2003/0114316 A1 | 6/2003 | Patel et al. |
| 2003/0130135 A1 | 7/2003 | Hou et al. |
| 2004/0014609 A1 | 1/2004 | Dalmazzone et al. |
| 2004/0082483 A1 | 4/2004 | Muller et al. |
| 2010/0210480 A1 | 8/2010 | Ballard et al. |
| 2010/0326660 A1 | 12/2010 | Ballard et al. |

(Continued)

FOREIGN PATENT DOCUMENTS

| | | |
|---|---|---|
| CN | 104232030 A | 12/2014 |
| CN | 105623629 A | 6/2016 |

(Continued)

OTHER PUBLICATIONS

Jitendra K. Satyarthi, D. Srinivas, Selective epoxidation of methyl soyate over alumina-supported group VI metal oxide catalysts, Applied Catalysts A: Gerneral 401 (2011) 189-198. (Year: 2011).*

(Continued)

*Primary Examiner* — Jeffrey D Washville
(74) *Attorney, Agent, or Firm* — Osha Bergman Watanabe & Burton LLP

(57) ABSTRACT

An invert oil-based mud (OBM) may include an oleaginous continuous phase, an aqueous internal phase, and an emulsifier. The emulsifier may include one or more of the group consisting of epoxidized methyl oleate, epoxidized methyl linoleate, and epoxidized methyl α-linolenate. The invert OBM may contain the emulsifier in an amount of the range of 0.1 to 10 wt. % (weight percent), relative to the total weight of the OBM.

17 Claims, 4 Drawing Sheets

(56) References Cited

U.S. PATENT DOCUMENTS

| | | | |
|---|---|---|---|
| 2013/0303410 A1 | 11/2013 | Wagle et al. | |
| 2014/0336086 A1* | 11/2014 | Frenkel | C09K 8/12 |
| | | | 507/136 |
| 2015/0014062 A1 | 1/2015 | Napierala et al. | |
| 2016/0289529 A1 | 10/2016 | Nguyen | |
| 2017/0191008 A1 | 7/2017 | Baseeth | |
| 2019/0169492 A1 | 6/2019 | Hill et al. | |

FOREIGN PATENT DOCUMENTS

| | | |
|---|---|---|
| CN | 105713591 A | 6/2016 |
| EP | 1346006 B1 | 12/2014 |
| WO | 2014001192 A1 | 1/2014 |
| WO | 2020011378 A1 | 1/2020 |

OTHER PUBLICATIONS

Sharma, Brajendra K. et al., "Oxidation, friction reducing, and low temperature properties of epoxy fatty acid methyl esters", Green Chem, The Royal Society of Chemistry, vol. 9, Feb. 2007, pp. 469-474 (6 pages).

International Search Report and Written Opinion issued in corresponding International Patent Application No. PCT/US2020/046410, dated Apr. 16, 2021 (15 pages).

Clemente, Tom et al., "Soybean Oil: Genetic Approaches for Modification of Functionality and Total Content: Figure 1", Plant Physiology, American Society of Plant Biologists, vol. 151, No. 3, 2009, pp. 1030-1040 (11 pages).

Sahoo, Sushanta K. et al., "Toughened Bio-Based Epoxy Blend Network Modified with Transesterified Epoxidized Soybean Oil: Synthesis and Characterization", RSC Advances, vol. 5, No. 18, 2015, pp. 13674-13691 (18 pages).

\* cited by examiner

EPOXIDIZED FATTY ACID METHYL ESTER AS PRIMARY EMULSIFIER FOR INVERT EMULSION OIL BASED MUD

BACKGROUND

Wellbore drilling operations may use wellbore fluids for multiple purposes including, for example, cooling the drill bit and transporting wellbore cuttings to the surface. Drilling fluids are also used to reduce friction between the drill string and the casing or the wellbore wall by functioning as a lubricating medium. Drilling fluids can be divided into a variety of categories including, for example, oil-based drilling fluids and water-based drilling fluids. Additives may be included to enhance the properties of the fluids.

Although water-based muds (WBMs) are often preferred due to environmental concerns that are associated with oil-based muds (OBMs), they may not be viable for use in certain high pressure and high temperature (HPHT) sections of a wellbore. This leads to the employment of OBMs, including invert emulsion OBMs, which may be more stable under such conditions. OBMs can also provide improved shale inhibition over WBMs and so are also preferred when drilling wellbore sections that contain reactive shale. Invert emulsion OBMs may be formulated to include additives, such as emulsifiers, which aid in the formation of a stable water-in-oil (W/O) emulsion, and rheology modifiers, which allow for tuning the rheological properties of the fluid.

SUMMARY

This summary is provided to introduce a selection of concepts that are further described in the detailed description. This summary is not intended to identify key or essential features of the claimed subject matter, nor is it intended to be used as an aid in limiting the scope of the claimed subject matter.

In one aspect, embodiments disclosed relate to an invert oil-based mud (OBM) that includes an oleaginous continuous phase, an aqueous internal phase, and an emulsifier. The emulsifier may include one or more of the group consisting of epoxidized methyl oleate, epoxidized methyl linoleate, and epoxidized methyl α-linolenate.

In another aspect, embodiments disclosed relate to methods of using an invert oil-based mud (OBM) in a wellbore that include introducing the invert OBM into the wellbore. The invert OBM may include an oleaginous continuous phase; an aqueous internal phase; and an emulsifier. The emulsifier may include one or more selected from the group consisting of epoxidized methyl oleate, epoxidized methyl linoleate, and epoxidized methyl alpha-linolenate.

In a further aspect, embodiments disclosed relate to methods of preparing an invert oil-based mud (OBM), the methods including forming an emulsifier by epoxidizing linseed oil and transesterifying the epoxidized linseed oil with methanol, and mixing the emulsifier with an oleaginous phase, and an aqueous phase.

Other aspects and advantages of the claimed subject matter will be apparent from the description, the drawings, and the claims that follow.

DETAILED DESCRIPTION

Figure 1A:
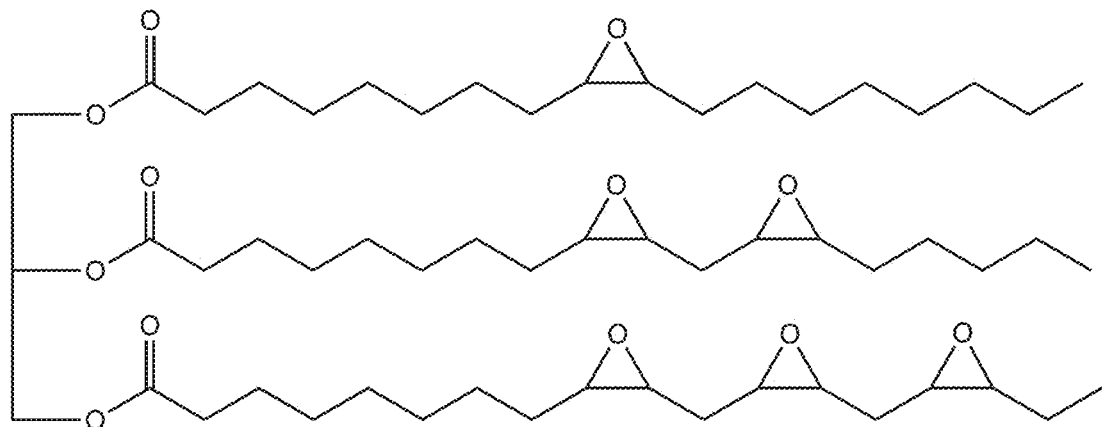
FIGS. 1A-B depict the chemical structures of an epoxidized triglyceride (FIG. 1A) and epoxidized fatty acid methyl esters (FIG. 1B) of one or more embodiments, which are derived from linseed oil.

Embodiments in accordance with the present disclosure generally relate to emulsifiers and their preparation, wellbore fluids that contain said emulsifiers, and methods of using said wellbore fluids. Generally, the emulsifiers of one or more embodiments disclosed comprise one or more epoxidized fatty acid esters.

As discussed above, invert emulsion OBMs may be used as drilling fluids for certain high pressure and high temperature (HPHT) sections of a wellbore due to their relative stability under such conditions. In order to provide this stability, the invert emulsion OBMs may include emulsifiers that aid the formation of a stable emulsion between oleaginous and non-oleaginous phases. Emulsifiers are a type of surfactant that generally have a hydrophilic head group and a hydrophobic tail (for example, a long carbon-containing chain). The combination of both hydrophilic and hydrophobic groups enables an emulsifier to reduce the interfacial tension between oleaginous and non-oleaginous phases and increase the emulsion stability of an invert emulsion OBM. This stabilization is generally provided by a "primary" emulsifier. Further "secondary" emulsifiers may be utilized to consolidate the stability of the dispersed phase or the overall emulsion stability.

Emulsifiers

Emulsifiers in accordance with one or more embodiments of the present disclosure may comprise one or more epoxidized fatty acid esters. These epoxidized fatty acid esters may be derived from a vegetable oil. The vegetable oil of some embodiments may be a triglyceride extracted from a plant. A triglyceride is an ester of glycerol and three fatty acids. Depending on the plant from which it is derived, a vegetable oil may contain a mixture of different types of fatty acids, including, for example, saturated, mono unsaturated, poly unsaturated, omega 3, omega 6, and omega 9 fatty acids. The presence of these different types of fatty acids makes vegetables a promising source for emulsifiers for drilling fluids. In some embodiments, the emulsifiers of the present disclosure may be derived from unused or unprocessed vegetable oils, such as virgin, fresh, or raw oils. In other embodiments, the emulsifiers of the present disclosure may be derived from waste vegetable oils that have been used for a different process, including cooking and other food preparations, prior to the preparation of the emulsifiers.

Emulsifiers in accordance with one or more embodiments of the present disclosure may contain epoxidized fatty acid esters that are derived from linseed oil. Linseed oil (which is also commonly known as flaxseed oil) is a natural oil that is derived from the seeds of the flax plant. It is widely used as an impregnator for various materials, as a drying oil or varnish, as a pigment binder, as a plasticizer, and as a nutritional supplement. Linseed oil comprises a triglyceride containing three different unsaturated fatty acids, namely oleic, linoleic acid and α-linolenic acid. Linseed oil may further contain smaller amounts of saturated fatty acids, such as palmitic acid and stearic acid, in addition to one or more unsaturated fatty acids.

The emulsifiers of one or more embodiments particularly comprise one or more epoxidized fatty acid esters. These epoxidized fatty acid esters may be prepared by first epoxidizing an unsaturated triglyceride to give an epoxidized triglyceride. Where, for instance, the triglyceride is linseed oil, the resulting epoxidized triglyceride may be epoxidized linseed oil as depicted in FIG. 1A. The epoxidized triglyceride may contain fatty acids having a carbon chain ranging in length from C6 to C32. For example, the epoxidized triglyceride may contain fatty acids having a carbon chain having a length ranging from a lower limit of any of 6, 8, 10, 12, 14, 16, and 18 carbons to an upper limit of any of 18, 20, 22, 24, 26, 28, 30, and 32 carbons, where any lower limit can be used in combination with any mathematically-compatible upper limit. Transesterifying the epoxidized triglyceride by reaction with an alcohol yields the corresponding epoxidized fatty acid esters. The particular alcohol used for the transesterification may not be particularly limited. In some embodiments, the alcohol may be one or more selected from the group consisting of methanol, ethanol, propanols, butanols, petanols, and isomers and derivatives thereof. In particular embodiments, the alcohol may be methanol, and the resulting epoxidized fatty acid esters may be epoxidized fatty acid methyl esters ("EME-FA").

Figure 1B:
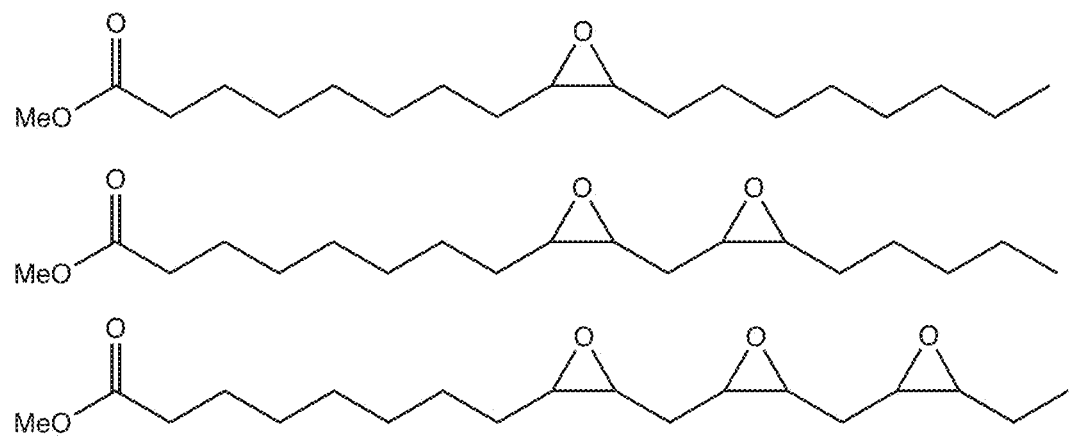

In embodiments where the triglyceride is linseed oil and the alcohol is methanol, the resulting emulsifier will comprise the epoxidized methyl ester of oleic acid (also known as epoxidized methyl oleate), the epoxidized methyl ester of linoleic acid (also known as epoxidized methyl linoleate), and the epoxidized methyl ester of α-linolenic acid (also known as epoxidized methyl α-linolenate), as depicted in FIG. 1B. In some embodiments, the EME-FA may be a commercial product, such as VIKOFLEX® 9010 (Arkema; King of Prussia, Pa.).

The emulsifier of one or more embodiments may comprise an ester of oleic acid, an ester of linoleic acid, and an ester of α-linolenic acid. In some embodiments, the emulsifier may consist essentially of an ester of oleic acid, an ester of linoleic acid, and an ester of α-linolenic acid. In some embodiments, the emulsifier may consist of an ester of oleic acid, an ester of linoleic acid, and an ester of α-linolenic acid.

In embodiments where the emulsifier is derived from linseed oil, the emulsifier may comprise an ester of oleic acid, an ester of linoleic acid, and an ester of α-linolenic acid, in relative amounts that reflect the content of each of oleic acid, linoleic acid, and α-linolenic acid in the linseed oil.

The emulsifier of one or more embodiments may contain an ester of oleic acid in an amount of the range of about 1 to 30% by weight (wt. %). For example, the emulsifier may contain the ester of oleic acid in an amount ranging from a lower limit of any of 1, 2, 5, 10, 12, 15, 18, and 20 wt. % to an upper limit of any of 10, 12, 15, 18, 20, 22, 25, and 30 wt. %, where any lower limit can be used in combination with any mathematically-compatible upper limit.

The emulsifier of one or more embodiments may contain an ester of linoleic acid in an amount of the range of about 1 to 30 wt. %. For example, the emulsifier may contain the ester of linoleic acid in an amount ranging from a lower limit of any of 1, 2, 5, 10, 12, 15, 18, and 20 wt. % to an upper limit of any of 10, 12, 15, 18, 20, 22, 25, and 30 wt. %, where any lower limit can be used in combination with any mathematically-compatible upper limit.

The emulsifier of one or more embodiments may contain an ester of α-linolenic acid in an amount of the range of about 30 to about 70 wt. %. For example, the emulsifier may contain the ester of α-linolenic acid in an amount ranging from a lower limit of any of 30, 35, 40, 45, 50, 55, and 60 wt. % to an upper limit of any of 40, 45, 50, 55, 60, 65, and 70 wt. %, where any lower limit can be used in combination with any mathematically-compatible upper limit.

Wellbore Fluids

One or more embodiments of the present disclosure relate to wellbore fluids and may include, for example, water-based wellbore fluids and oil-based wellbore fluids. In particular embodiments, the wellbore fluids may be oil-based emulsion fluids (otherwise known in the industry as a water-in-oil emulsion or W/O emulsion). The wellbore fluids may be drilling fluids, such as oil-based drilling muds (OBMs).

Oil-based wellbore fluids of one or more embodiments may have an oleaginous base fluid. The oleaginous fluid may be a natural or synthetic oil. In one or more embodiments, the oleaginous fluid may be one or more of diesel oil, mineral oil, polyalphaolefins, siloxanes, organosiloxanes, fatty acid esters, and mixtures thereof. Safra oil is a highly de-aromatized aliphatic solvent in the class of kerosene.

Wellbore fluids of one or more embodiments may be emulsions that comprise both an oleaginous external phase and a non-oleaginous internal phase. The oleaginous external phase may comprise one or more of the oleaginous fluids described previously. The non-oleaginous internal phase may be an aqueous fluid. The aqueous fluid may include at least one of fresh water, synthetic or natural seawater, synthetic or natural brine, formation water, production water, brackish water, each of which may contain water-soluble organic compounds or minerals, or both, and mixtures thereof. The aqueous fluid may be fresh water that is formulated to contain various salts. The salts may include, but are not limited to, alkali metal halides and hydroxides. In one or more embodiments of the wellbore fluid disclosed, the brine may be any of seawater, aqueous solutions where the salt concentration is less than that of seawater, or aqueous solutions where the salt concentration is greater than that of seawater. Salts that may be found in seawater may include salts that produce disassociated ions of sodium, calcium, aluminium, magnesium, potassium, strontium, lithium, halides, carbonates, chlorates, bromates, nitrates, oxides, and phosphates, among others. In some embodiments, the brine may include one or more of the group consisting of an alkali metal halide, an alkali metal carboxylate salt, an alkaline earth metal halide, and an alkaline earth metal carboxylate salt. In particular embodiments, the brine may comprise calcium chloride. Any of the aforementioned salts may be included in brine.

In one or more embodiments, the density of aqueous fluid, and, in turn, the wellbore fluid, may be controlled by increasing the salt concentration. The maximum concentration is determined by the solubility of the salt.

In some embodiments, wellbore fluids may be invert emulsions that have an oleaginous external phase and a non-oleaginous internal phase. The invert emulsion of one or more embodiments may contain a volume ratio of the oleaginous phase to the non-oleaginous phase ranging from about 30:70 to about 99:1. For example, the invert emulsion may have a volume ratio of the oleaginous phase to the non-oleaginous phase ranging from a lower limit of any of 30:70, 40:60, 50:50, 60:40, 70:30, 80:20, and 90:10 to an upper limit of any 40:60, 50:50, 60:40, 70:30, 80:20, 90:10, and 99:1, where any lower limit can be used in combination with any mathematically-compatible upper limit.

In one or more embodiments, wellbore fluids may contain one or more of the emulsifiers described previously. The wellbore fluid of one or more embodiments may comprise one of the previously-discussed emulsifiers as a primary emulsifier in an amount ranging from about 0.1 to about 20 vol. %. For example, the wellbore fluid may contain the emulsifier in an amount ranging from a lower limit of any of 0.1, 0.3, 0.5, 0.7, 1.0, 1.2, 1.5, 2.0, 2.5, 3.0, 4.0, 5.0, and 10.0 vol. % to an upper limit of any of 1.0, 2.0, 3.0, 4.0, 5.0, 6.0, 7.0, 10.0, 12.5, 15.0, 17.5, and 20.0 vol. %, where any lower limit can be used in combination with any mathematically-compatible upper limit. In particular embodiments, the wellbore fluid may contain the emulsifier in an amount of about 1.0 to about 6.0 vol. %.

The wellbore fluid of one or more embodiments may comprise one of the previously-discussed emulsifiers as a primary emulsifier in an amount ranging from about 0.1 to about 10 wt. %. For example, the wellbore fluid may contain the emulsifier in an amount ranging from a lower limit of any of 0.1, 0.3, 0.5, 0.7, 1.0, 1.2, 1.5, 2.0, 2.5, 3.0, and 5.0 wt. % to an upper limit of any of 1.0, 1.5, 2.0, 2.5, 3.0, 3.5, 4.0, 5.0, 7.5, and 10 wt. %, where any lower limit can be used in combination with any mathematically-compatible upper limit. In particular embodiments, the wellbore fluid may contain the emulsifier in an amount of about 1.0 to about 3.0 wt. %.

In one or more embodiments, wellbore fluids may contain an additional, or secondary, emulsifier. The secondary emulsifier may be utilized to consolidate the stability of the dispersed phase or the overall emulsion. The secondary emulsifier of one or more embodiments is not particularly limited but, as would be understood by a person of ordinary skill in the art, is generally selected to be compatible with the primary emulsifier. In some embodiments, the secondary emulsifier may be EZ MUL® (Halliburton; Houston, Tex.).

The wellbore fluid of one or more embodiments may comprise a secondary emulsifier in an amount ranging from about 0.1 to about 10% by volume (vol. %). For example, the wellbore fluid may contain the secondary emulsifier in an amount ranging from a lower limit of any of 0.1, 0.3, 0.5, 0.7, 1.0, 1.2, 1.5, 2.0, 2.5, 3.0, and 5.0 vol. % to an upper limit of any of 1.0, 1.5, 2.0, 2.5, 3.0, 3.5, 4.0, 5.0, 7.5, and 10 vol. %, where any lower limit can be used in combination with any mathematically-compatible upper limit. In particular embodiments, the wellbore fluid may contain the secondary emulsifier in an amount of about 0.5 to about 2.0 vol. %.

The wellbore fluid of one or more embodiments may comprise a secondary emulsifier in an amount ranging from about 0.1 to about 5 wt. %. For example, the wellbore fluid may contain the secondary emulsifier in an amount ranging from a lower limit of any of 0.1, 0.2, 0.3, 0.4, 0.5, 0.6, 0.7, 0.8, 1.0, 1.2, 1.5, 2.0, 2.5, and 3.0 wt. % to an upper limit of any of 0.5, 0.6, 0.8, 1.0, 1.2, 1.4, 1.6, 1.8, 2.0, 2.5, 3.0, 3.5, 4.0, 4.5, and 5.0 wt. %, where any lower limit can be used in combination with any mathematically-compatible upper limit. In particular embodiments, the wellbore fluid may contain the secondary emulsifier in an amount of about 0.1 to about 1.0 wt. %.

Further, other additives may be included in the wellbore fluids of the present disclosure. Such additives may include, for instance, one or more of the group consisting of weighting agents, pH adjusting agents, rheology modifiers (or viscosifiers), wetting agents, corrosion inhibitors, oxygen scavengers, anti-oxidants, biocides, surfactants, dispersants, interfacial tension reducers, mutual solvents, thinning agents, and combinations thereof. The identities and use of the aforementioned additives are not particularly limited. One of ordinary skill in the art will, with the benefit of this disclosure, appreciate that the inclusion of a particular additive will depend upon the desired application and properties of a given wellbore fluid.

Weighting agents suitable for use in the wellbore fluids of one or more embodiments include, for example, bentonite, barite, dolomite, calcite, aragonite, iron carbonate, zinc carbonate, manganese tetroxide, zinc oxide, zirconium oxide, hematite, ilmenite, lead carbonate, and combinations thereof.

The pH adjusting agents that are included in the wellbore fluids of one or more embodiments may be one or more alkaline compounds. In one or more embodiments, suitable alkaline compounds include alkali metal and alkaline metal salts, such as lime, soda ash, sodium hydroxide, and potassium hydroxide, and combinations thereof.

The wellbore fluid of one or more embodiments may comprise a pH adjusting agent in an amount ranging from about 0.1 to 5 wt. %. For example, the wellbore fluid may contain the pH adjusting agent in an amount ranging from a lower limit of any of 0.1, 0.2, 0.3, 0.4, 0.5, 0.6, 0.7, 0.8, 1.0, 1.2, 1.5, 2.0, 2.5, and 3.0 wt. % to an upper limit of any of 0.5, 0.6, 0.8, 1.0, 1.2, 1.4, 1.6, 1.8, 2.0, 2.5, 3.0, 3.5, 4.0, 4.5, and 5.0 wt. %, where any lower limit can be used in combination with any mathematically-compatible upper limit. In particular embodiments, the wellbore fluid may contain the pH adjusting agent in an amount of about 0.5 to about 1.5 wt. %.

The viscosifiers that are included in the wellbore fluids of one or more embodiments may be selected from the group consisting of organophilic clays, hectorite clays, dimeric and trimeric fatty acids, polyamines, and sepiolite. In some embodiments, the viscosifier may be GELTONE® II (Halliburton; Houston, Tex.).

The wellbore fluid of one or more embodiments may comprise a viscosifier in an amount ranging from about 0.1 to about 5 wt. %. For example, the wellbore fluid may contain the viscosifier in an amount ranging from a lower limit of any of 0.1, 0.2, 0.3, 0.4, 0.5, 0.6, 0.7, 0.8, 1.0, 1.2, 1.5, 2.0, 2.5, and 3.0 wt. % to an upper limit of any of 0.5, 0.6, 0.8, 1.0, 1.2, 1.4, 1.6, 1.8, 2.0, 2.5, 3.0, 3.5, 4.0, 4.5, and 5.0 wt. %, where any lower limit can be used in combination with any mathematically-compatible upper limit. In particular embodiments, the wellbore fluid may contain the viscosifier in an amount of about 0.1 to about 1.0 wt. %.

The filtration control agents that are included in the wellbore fluids of one or more embodiments may be selected from the group consisting of modified lignites, asphalts or gilsonites, and nonaqueous polymeric fluids. In some embodiments, the filtration control agent may be DURATONE® HT (Halliburton; Houston, Tex.)

The wellbore fluid of one or more embodiments may comprise a filtration control agent in an amount ranging from about 0.1 to about 5 wt. %. For example, the wellbore fluid may contain the filtration control agent in an amount ranging from a lower limit of any of 0.1, 0.2, 0.3, 0.4, 0.5, 0.6, 0.7, 0.8, 1.0, 1.2, 1.5, 2.0, 2.5, and 3.0 wt. % to an upper limit of any of 0.5, 0.6, 0.8, 1.0, 1.2, 1.4, 1.6, 1.8, 2.0, 2.5, 3.0, 3.5, 4.0, 4.5, and 5.0 wt. %, where any lower limit can be used in combination with any mathematically-compatible upper limit. In particular embodiments, the wellbore fluid may contain the filtration control agent in an amount of about 0.5 to about 1.5 wt. %.

Figure 2:
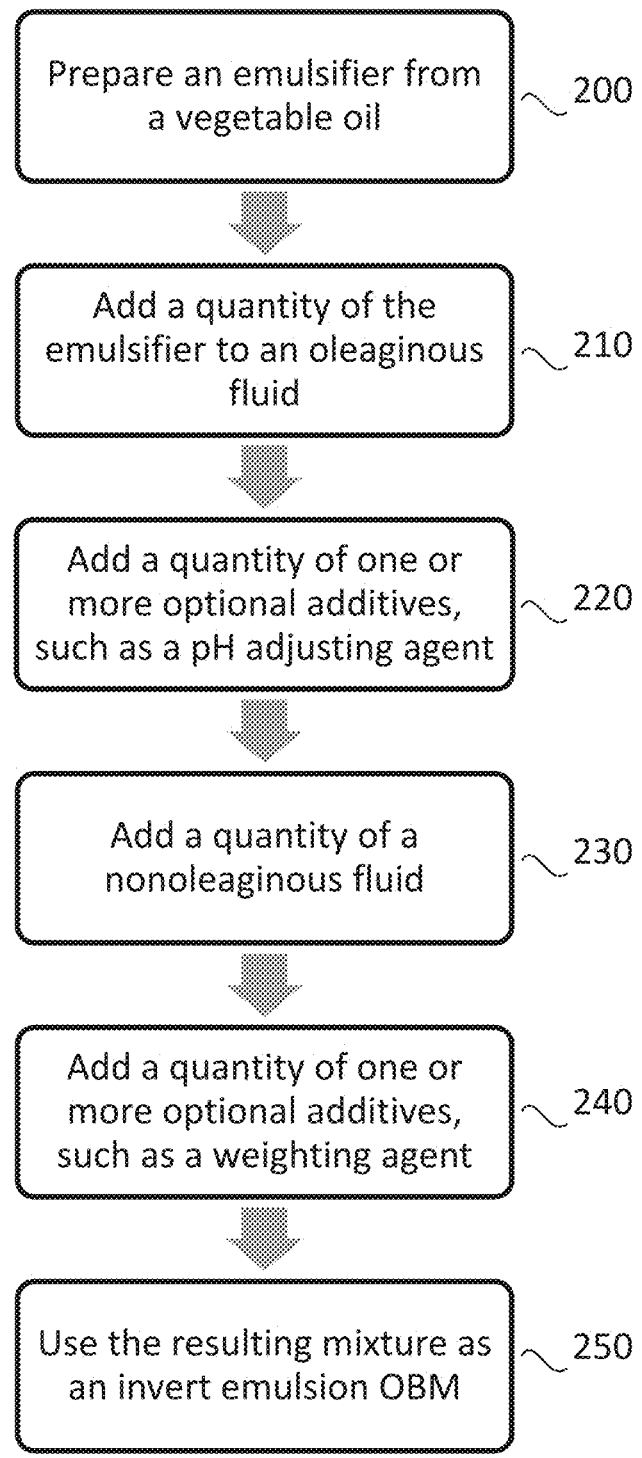
FIG. 2 is a schematic representation of a method of producing an invert emulsion OBM of one or more embodiments.

A method of preparing an invert OBM of one or more embodiments is depicted by FIG. 2. All components and quantities discussed in relation to said method correspond to those discussed previously. At 200, an emulsifier is prepared from a vegetable oil. For example, the emulsifier may be prepared from linseed oil as discussed previously. In one or more embodiments, the emulsifier may comprise one or more epoxidized fatty acid esters, such as an ester of epoxidized oleic acid, an ester of epoxidized linoleic acid, and an ester of epoxidized α-linolenic acid.

At 210, a quantity of the emulsifier is added to an oleaginous base fluid. At 220, a quantity of an optional additive, such as a pH adjusting agent, may also be added to the oleaginous base fluid. At 230, a quantity of a nonoleaginous fluid is added to the oleaginous fluid to which the previously mentioned components have been added. At 240, a quantity of an additive, such as a weighting agent, is added to the aforementioned components. At 250, the inverted oil-based drilling fluid mixed with the previously mentioned components is used in a wellbore drilling operation to drill a wellbore in a subterranean zone. For example, multiple barrels of the oil-based drilling fluid are prepared, each barrel mixed with the previously mentioned components. The multiple barrels are flowed through a subterranean zone while drilling a wellbore in the subterranean zone.

The physical properties of a wellbore fluid are important in determining the suitability of the fluid for a given application.

The wellbore fluid of one or more embodiments may have a density that is greater than 60 lbs/ft$^3$ (pounds per cubic foot). For example, the wellbore fluid may have a density that is of an amount ranging from a lower limit of any of 60, 62, 64, 66, 68, 70, 75, and 80 lbs/ft$^3$ to an upper limit of any of 66, 68, 70, 75, 80, 90, and 100 lbs/ft$^3$, where any lower limit can be used in combination with any mathematically-compatible upper limit.

The wellbore fluid of one or more embodiments may have an electrical stability that is 300 V (volts) or more, 320 V or more, or 340 V or more. For example, the wellbore fluid may have an electrical stability that is of an amount ranging from a lower limit of any of 280, 290, 300, 310, 320, 330, 340, and 350 V to an upper limit of any of 340, 350, 360, 370, 380, 390, and 400 V, where any lower limit can be used in combination with any mathematically-compatible upper limit.

Rheological features, such as plastic viscosity (PV), yield point (YP), initial gel strength, and final gel strength, can be determined for a wellbore fluid. The values described may be determined for a wellbore fluid after hot-rolling at, for instance, 300° F. for 16 h (hours) under a pressure of 500 psi (pounds per square inch). The values were obtained from a viscometer at dial readings of 600 rpm (revolutions per minute) and 300 rpm. To measure the initial and final gel strength of a wellbore fluid, a viscometer can be operated at 600 rpm for 10 s (seconds) and then switched off for 10 s and 10 min (minutes), respectively. Afterward, the viscometer can be turned to a revolution speed of 3 rpm to provide the gel strength reading.

The YP and PV are parameters from the Bingham Plastic rheology (BP) model. The plastic viscosity of a fluid is a measure of the resistance of the fluid to flow. For instance, drilling fluids that have a reduced plastic viscosity, compared to drilling fluids with a greater PV value, have the capacity to drill more quickly. Plastic viscosity is dependent on both the solid content of a fluid and temperature. The wellbore fluid of one or more embodiments may have a plastic viscosity ranging from about 5 to about 60 cP (centipoise). For example, the wellbore fluid may have a plastic viscosity that ranges from a lower limit of any of 5, 10, 15, 20, 25, 30, 35, and 40 cP to an upper limit of any of 30, 35, 40, 45, 50, 55, and 60 cP, where any lower limit can be used in combination with any mathematically-compatible upper limit.

The YP is determined by extrapolating the BP model to a shear rate of zero; it represents the stress required to move the fluid. The yield point is the resistance of a fluid to initiate movement and is an assessment of the strength of the attractive forces between the colloidal particles of the fluid. The yield point, for instance, demonstrates the capability of a drilling fluid to raise shale cuttings out of a wellbore under dynamic conditions. A fluid with a greater yield point may provide a better carrying capacity as compared to a fluid with similar density and reduced yield point. The wellbore fluid of one or more embodiments may have a yield point ranging from about 5 to about 60 lb/100 ft$^2$ (pounds per 100 square feet). For example, the wellbore fluid may have a yield point that ranges from a lower limit of any of 5, 10, 15, 20, 25, 30, 35, and 40 lb/100 ft$^2$ to an upper limit of any of 30, 35, 40, 45, 50, 55, and 60 lb/100 ft$^2$, where any lower limit can be used in combination with any mathematically-compatible upper limit.

The wellbore fluid of one or more embodiments may have an initial gel strength, after 10 seconds, ranging from about 10 to about 50 lbs/100 ft$^2$. For example, the wellbore fluid may have an initial gel strength that ranges from a lower limit of any of 10, 15, 20, 25, 30, and 35 lbs/100 ft$^2$ to an upper limit of any of 30, 35, 40, 45, and 50 lbs/100 ft$^2$, where any lower limit can be used in combination with any mathematically-compatible upper limit.

The wellbore fluid of one or more embodiments may have a final gel strength, after 10 minutes, ranging from about 10 to about 60 lbs/100 ft$^2$. For example, the wellbore fluid may have a final gel strength that ranges from a lower limit of any of 10, 15, 20, 25, 30, 35, and 40 lbs/100 ft$^2$ to an upper limit of any of 35, 40, 45, 50, 55, and 60 lbs/100 ft$^2$, where any lower limit can be used in combination with any mathematically-compatible upper limit.

The wellbore fluid of one or more embodiments may have a 3-rpm viscometer reading ranging from about 1 to about 30 cP. For example, the wellbore fluid may have a plastic viscosity that ranges from a lower limit of any of 1, 2, 3, 4, 5, 6, 8, 10, 12, and 15 cP to an upper limit of any of 6, 8, 10, 12, 15, 20, 25, and 30 cP, where any lower limit can be used in combination with any mathematically-compatible upper limit.

The wellbore fluid of one or more embodiments may have a 6-rpm viscometer reading ranging from about 1 to about 30 cP. For example, the wellbore fluid may have a plastic viscosity that ranges from a lower limit of any of 1, 2, 3, 4, 5, 6, 8, 10, 12, and 15 cP to an upper limit of any of 6, 8, 10, 12, 15, 20, 25, and 30 cP, where any lower limit can be used in combination with any mathematically-compatible upper limit.

The apparent viscosity of a fluid is directly related to the swelling rate of the fluid in the presence of an inhibition medium. Therefore, a low apparent viscosity demonstrates that the fluid may have a reduced interaction with clay. The wellbore fluid of one or more embodiments may have an apparent viscosity ranging from about 10 to about 150 cP. For example, the wellbore fluid may have an apparent viscosity that ranges from a lower limit of any of 10, 15, 20, 25, 30, 35, 40, 45, 50, 55, 60, 65, 70, 75, 80, 90 and 100 cP to an upper limit of any of 20, 30, 40, 50, 60, 70, 80, 90, 100, 110, 120, 130, 140, and 150 cP, where any lower limit can be used in combination with any mathematically-compatible upper limit.

Methods

Wellbore fluids of one or more embodiments may be introduced into a wellbore or subterranean formation using techniques known to a person of ordinary skill in the art. The wellbore fluids of one or more embodiments may be used as one or more of a drilling or drill-in fluid during the drilling of a wellbore. The oil-based drilling fluid emulsified with the previously mentioned components may be used in a wellbore drilling operation to drill a wellbore in a subterranean zone. For example, multiple barrels of the oil-based drilling fluid may be prepared, each barrel mixed with the previously discussed components. The multiple barrels are introduced into a subterranean zone while drilling the wellbore in the subterranean zone.

EXAMPLES

The following examples are merely illustrative and should not be interpreted as limiting the scope of the present disclosure.

Materials and Synthesis:

The fatty acid methyl esters (hereafter "EME-FA") used in these examples was VIKOFLEX® 9010 (Arkema; King of Prussia, Pa.), which contains epoxidized methyl oleate, epoxidized methyl linoleate, and epoxidized methyl alpha-linoleate.

In order to ascertain the ability of the EME-FA to function as a primary emulsifier, invert OBMs having the compositions detailed in Table 1 were prepared. In the examples, 12 ppb (pounds per barrel) of the primary emulsifiers are used to formulate 80 pcf (per cubic feet) invert-emulsion oil based muds using Safra-oil as a base oil. Safra oil is a highly de-aromatized aliphatic solvent in the class of kerosene. The oil-water ratio is 70:30 by volume. "mL" means millilitres and "g" means grams.

TABLE 1

Compositions of exemplary drilling muds

| Formulation | Example 1 | Comparative Example 1 |
|---|---|---|
| Safra oil (mL) | 218 | 218 |
| EME-FA (mL) | 12 | 0 |
| INVERMUL ® (mL) | 0 | 12 |
| EZ MUL ® (mL) | 4 | 4 |
| Lime (g) | 6 | 6 |
| GELTONE ® (g) | 4 | 4 |
| DURATONE ® (g) | 6 | 6 |
| Brine (mL) (61 g $CaCl_2$ in 85 mL of water) | 85 | 85 |
| Barite (g) | 161 | 161 |

Characterization:

The OBM dispersions were hot rolled at 300° F. for 16 h under a pressure of 500 psi. After hot rolling, the OBMs were cooled to room temperature and a OFITE Model 900 viscometer (OFI Testing Equipment, Inc.) was utilized for testing their rheology. The rheological properties of Example 1 and Comparative Example 1 were measured at 49° C. and are reported in Table 2.

TABLE 2

Rheological properties of exemplary OBMs

| Property | Example 1 | Comparative Example 1 |
|---|---|---|
| Plastic viscosity (PV) (cP) | 44.22 | 22.9 |
| Yield point (YP) (lbs/100 $ft^2$) | 39.9 | 9.2 |
| 10 sec gel strength (lbs/100 $ft^2$) | 31.3 | 5.2 |
| 10 min gel strength (lbs/100 $ft^2$) | 10.8 | 10.8 |
| Electrical stability (V) | 340 | 295 |

The rheological features such as the plastic viscosity (PV) and yield point (YP) were estimated by using the values obtained from the dial readings of the viscometer at 600 rpm and 300 rpm. To measure the 10-second (initial) gel strength and the 10-minute (final) gel strength of the OBMs, the viscometer was operated at 600 rpm for 10 s and then stopped for 10 s and 10 min, respectively. Afterward, the viscometer was operated at a revolution speed of 3 rpm and the dial reading was noted as the 10-sec and 10-min gel strength, respectively, in pounds per 100 $ft^2$.

Results and Discussion

The plastic viscosity and yield point are important properties that inform the suitability of an OBM for a given application. Table 2 indicates that the plastic viscosity and the yield point of a drilling mud significantly increase with the use of the EME-FA emulsifier as compared to the INVERMUL® emulsifier. This increased yield point indicates that Example 1 has an improved carrying capacity of cuttings as compared to Comparative Example 1. The inclusion of EME-FA only resulted in a small increase in plastic viscosity.

Figure 3:
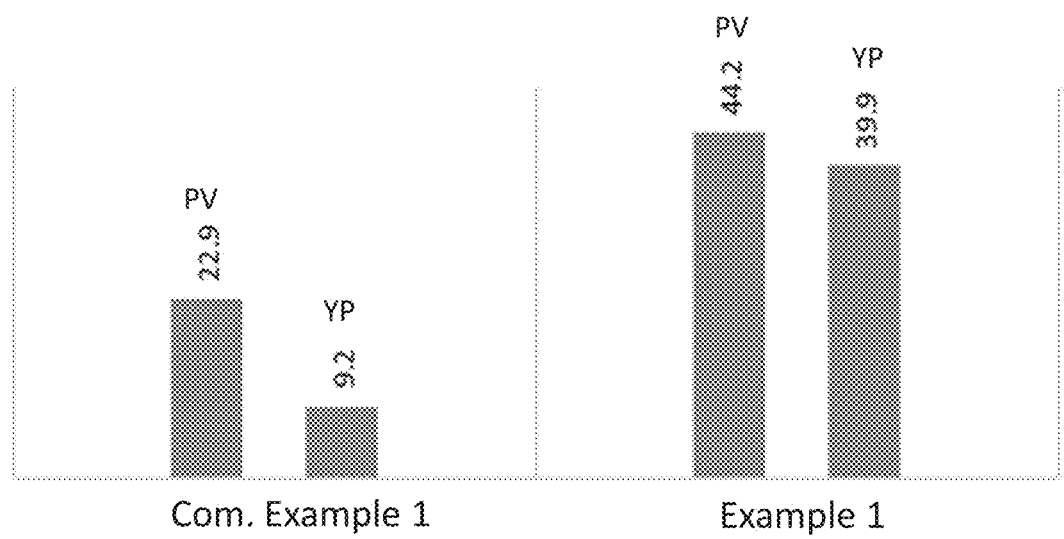
FIG. 3 is a graphical representation of the low-shear rheology of exemplary wellbore fluids.

The low shear rheology of a drilling mud reflects its ability to suspend a solid material under while the shear is minimized or ceased. The rheology of Example 1 and Comparative Example 1 at 3-rpm and 6-rpm is reported in Table 2 and depicted in FIG. 3. FIG. 3 shows comparatively that the use of the EME-FA prominently enhances the low shear rheology of an OBM, as compared to a conventional emulsifier such as INVERMUL®. Therefore, the addition of EME-FA provides an OBM having an enhanced solids-suspending capacity.

Figure 4:
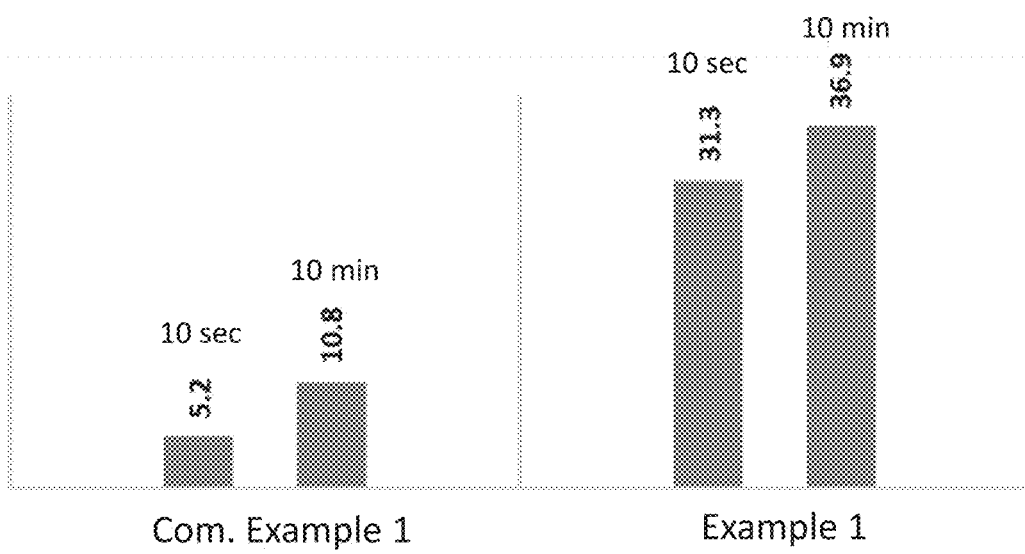
FIG. 4 is a graphical representation of the 10 second and 10 minute gel strength of exemplary wellbore fluids.

Similarly, the gel strength of a drilling mud reflects its ability to suspend a solid material under static conditions. It is a quantification of the attractive forces within the drilling mud system in the absence of flow. The gel strength of Example 1 and Comparative Example 1 is reported in Table 2 and depicted in FIG. 4, which demonstrate that the use of the EME-FA prominently enhances the gel strength of an OBM after both 10 s and 10 min, as compared to a conventional emulsifier. Therefore, the addition of EME-FA provides an OBM having an enhanced solids-suspending capacity.

Figure 5:
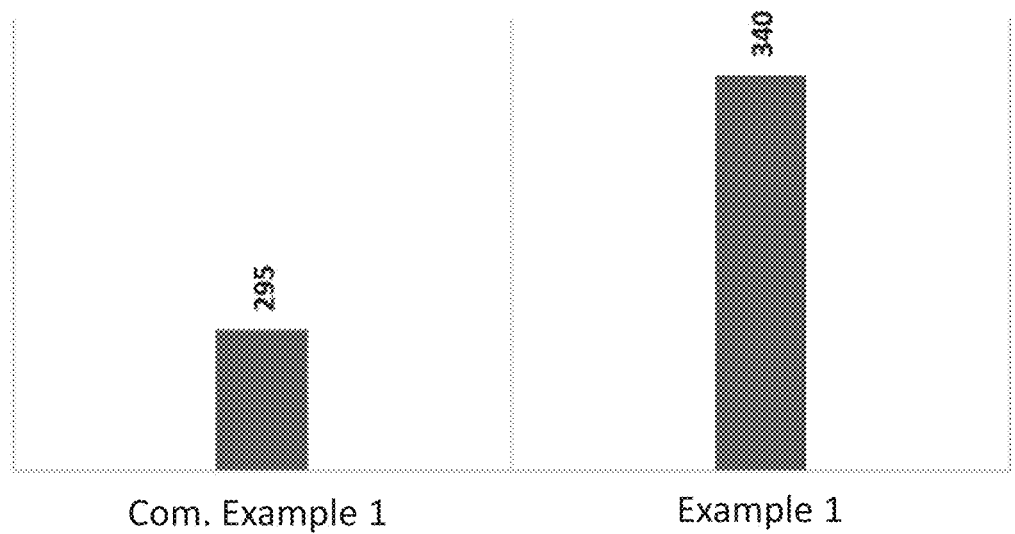
FIG. 5 is a graphical representation of the electrical stability of exemplary wellbore fluids.

Finally, the electrical stability of Example 1 and Comparative Example 1 is reported in Table 2 and depicted in FIG. 5. It is demonstrated that the use of the EME-FA prominently enhances the electrical stability of the invert OBM, as compared to a conventional emulsifier.

When either words "approximately" or "about" are used, this term may mean that there can be a variance in value of up to ±10%, of up to 5%, of up to 2%, of up to 1%, of up to 0.5%, of up to 0.1%, or up to 0.01%.

Although the preceding description has been described herein with reference to particular means, materials and embodiments, it is not intended to be limited to the particulars disclosed herein; rather, it extends to all functionally equivalent structures, methods and uses, such as those within the scope of the appended claims.

What is claimed is:

1. An invert oil-based mud (OBM), comprising:
   an oleaginous continuous phase;
   an aqueous internal phase; and
   an emulsifier comprising 1 to 30 wt. % epoxidized methyl oleate, 1 to 30 wt. % epoxidized methyl linoleate, and 30 to 70 wt. % epoxidized methyl α-linolenate.

2. The invert OBM according to claim 1, wherein the invert OBM contains the emulsifier in an amount of the range of 0.1 to 10 wt. % (weight percent), relative to the total weight of the OBM.

3. The invert OBM according to claim 1, wherein the invert OBM has a plastic viscosity of the range of 20 to 50 cP (centipoise).

4. The invert OBM according to claim 1, wherein the invert OBM has a yield point of the range of 20 to 50 lbs/100 ft$^2$ (pounds per 100 square feet).

5. The invert OBM according to claim 1, wherein the invert OBM has an initial gel strength after 10 seconds of the range of 20 to 40 lbs/100 ft$^2$.

6. The invert OBM according to claim 1, wherein the invert OBM has a final gel strength after 10 minutes of the range of 20 to 40 lbs/100 ft$^2$.

7. A method of using an invert oil-based mud (OBM) in a wellbore, comprising:
   introducing the invert OBM into the wellbore, the invert OBM comprising an oleaginous continuous phase; an aqueous internal phase; and an emulsifier, where the emulsifier comprises one or more of the group consisting of epoxidized methyl oleate, epoxidized methyl linoleate, and epoxidized methyl alpha-linolenate.

8. The method according to claim 7, wherein the emulsifier comprises epoxidized methyl oleate, epoxidized methyl linoleate, and epoxidized methyl α-linolenate.

9. The method according to claim 7, wherein the invert OBM contains the emulsifier in an amount of the range of 0.1 to 10 wt. %, relative to the total weight of the OBM.

10. The method according to claim 7, wherein the invert OBM has a plastic viscosity of the range of 20 to 50 cP.

11. The method according to claim 7, wherein the invert OBM has a yield point of the range of 20 to 50 lbs/100 ft$^2$.

12. The method according to claim 7, wherein the invert OBM has an initial gel strength after 10 seconds of the range of 20 to 40 lbs/100 ft$^2$.

13. The method according to claim 7, wherein the invert OBM has a final gel strength after 10 minutes of the range of 20 to 40 lbs/100 ft$^2$.

14. A method of preparing an invert oil-based mud (OBM), comprising:
   forming an emulsifier by epoxidizing linseed oil and transesterifying the epoxidized linseed oil with methanol; and
   mixing the emulsifier with an oleaginous phase and an aqueous phase.

15. The method according to claim 14, wherein the emulsifier comprises one or more selected from the group consisting of epoxidized methyl oleate, epoxidized methyl linoleate, and epoxidized methyl α-linolenate.

16. The method according to claim 15, wherein the emulsifier comprises epoxidized methyl oleate, epoxidized methyl linoleate, and epoxidized methyl α-linolenate.

17. The method according to claim 14, wherein the emulsifier is mixed in an amount such that the invert OBM contains the emulsifier in an amount of the range of 0.1 to 10 wt. % (weight percent), relative to the total weight of the OBM.

* * * * *